United States Patent [19] [11] 4,104,049
Maurer et al. [45] Aug. 1, 1978

[54] CHLORINE-SUBSTITUTED VINYLAMINOBENZOIC ACID COMPOUNDS AND PLANT GROWTH REGULANT COMPOSITIONS

[75] Inventors: Fritz Maurer; Hans-Jochem Riebel; Rolf Schröder, all of Wuppertal; Klaus Lürssen, Berg.Gladbach, all of Germany

[73] Assignee: Bayer Aktiengesellschaft, Leverkusen, Germany

[21] Appl. No.: 734,478

[22] Filed: Oct. 20, 1976

[30] Foreign Application Priority Data

Nov. 11, 1975 [DE] Fed. Rep. of Germany ....... 2550519

[51] Int. Cl.² .................. A01N 5/00; A01N 9/20; C07C 101/54; C07C 121/78
[52] U.S. Cl. .................. 71/76; 71/105; 71/111; 71/115; 71/118; 260/465 D; 260/518 A; 260/558 A; 560/43; 560/44; 560/47
[58] Field of Search .......... 260/465 D, 518 A, 471 R, 260/471 A, 558 A; 71/105, 111, 115, 118, 76; 560/43, 44, 47

[56] References Cited

U.S. PATENT DOCUMENTS

| 3,079,366 | 2/1963 | Boyle et al. | 260/465 X |
| 3,656,932 | 4/1972 | Scheurermann et al. | 71/105 |
| 3,726,662 | 4/1973 | Howe et al. | 71/103 |
| 3,981,717 | 9/1976 | Walworth | 71/105 |

Primary Examiner—Dolph H. Torrence
Attorney, Agent, or Firm—Burgess, Dinklage & Sprung

[57] ABSTRACT

Chlorine-substituted vinylaminobenzoic acid compounds of the formula

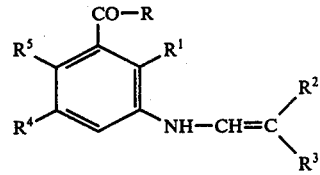

in which
  R is hydroxyl, alkoxy of from 1 to 4 carbon atoms or monoalkylamino of from 1 to 3 carbon atoms,
  $R^1$, $R^4$ and $R^5$ are individually selected from hydrogen and chlorine, provided that at least one of $R^1$, $R^4$ and $R^5$ is chlorine,
  $R^2$ is alkylcarbonyl of from 1 to 4 carbon atoms in the alkyl moiety or carbalkoxy of from 1 to 4 carbon atoms in the alkoxy moiety; and
  $R^3$ is cyano, alkylcarbonyl of from 1 to 4 carbon atoms in the alkyl moiety or carbalkoxy of from 1 to 4 carbon atoms in the alkoxy moiety exhibit outstanding plate growth regulating effects, e.g., the inhibition of vegetative plant growth.

22 Claims, No Drawings

CHLORINE-SUBSTITUTED VINYLAMINOBENZOIC ACID COMPOUNDS AND PLANT GROWTH REGULANT COMPOSITIONS

The present invention relates to certain new chlorine-substituted vinylaminobenzoic acid compounds, to plant-growth regulant compositions containing them, and to their use in methods for regulating plant growth.

It is known that 2-chloroethyltrimethylammonium chloride exhibits plant growth-regulating properties from U.S. Pat. No. 3,156,554. However, the activity of this compound is not always entirely satisfactory, especially when low amounts and low concentrations are used.

The present invention provides, as new compounds, the chlorine-substituted vinylaminobenzoic acid derivatives of the general formula

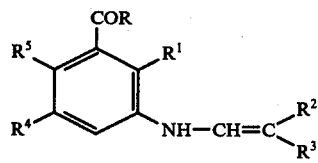

in which
R is hydroxyl, alkoxy of from 1 to 4 carbon atoms or monoalkylamino of from 1 to 3 carbon atoms,
$R^1$, $R^4$ and $R^5$, independently of one another, is hydrogen or chlorine, provided that at least one of these radicals is chlorine,
$R^2$ is alkylcarbonyl of from 1 to 4 carbon atoms in the alkyl part or carbalkoxy with 1 to 4 carbon atoms in the alkoxy group and
$R^3$ represents cyano, alkylcarbonyl with 1 to 4 carbon atoms in the alkyl part or carbalkoxy with 1 to 4 carbon atoms in the alkoxy group.

The present compounds exhibit strong plant growth-regulating properties.

Preferably, R represents hydroxyl, straight-chain or branched alkoxy with 1 to 3 carbon atoms (methoxy, ethoxy and n- or iso-propoxy may be mentioned specifically) or monomethylamino or monoethylamino, $R^2$ represents straight-chain or branched alkylcarbonyl with 1 to 3 carbon atoms in the alkyl part (methylcarbonyl, ethylcarbonyl, n-propylcarbonyl and iso-propylcarbonyl may be mentioned specifically) or carbethoxy, and $R^3$ represents cyano, straight-chain or branched alkylcarbonyl with 1 to 3 carbon atoms in the alkyl part or carbalkoxy with 1 to 3 carbon atoms in the alkoxy part (methylcarbonyl, ethylcarbonyl and n- or iso-propylcarbonyl, and carbomethoxy, carbethoxy, carbo-n-propoxy and carb-iso-propoxy may be mentioned specifically).

The present invention also provides a process for the preparation of a chlorine-substituted vinylaminobenzoic acid derivative of the formula (I), in which a chlorine-substituted aminobenzoic acid derivative of the general formula

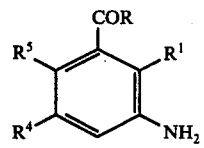

in which
R, $R^1$, $R^4$ and $R^5$ have the above-mentioned meanings, is reacted with a compound of the general formula

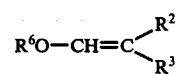

in which
$R^2$ and $R^3$ have the above-mentioned meanings and
$R^6$ represents alkyl with 1 to 4 carbon atoms, especially methyl or ethyl,
if appropriate in the presence of a solvent or diluent.

Surprisingly, the chlorine-substituted vinylaminobenzoic acid derivatives according to the invention exhibit a substantially greater plant growth-regulating action than 2-chloroethyltrimethylammonium chloride, known from the state of the art, which is chemically the nearest active compound of the same type of action. An aspect to be singled out above all is that the compounds according to the invention are substantially more suitable for the inhibition of vegetative plant growth than is 2-chloroethyltrimethylammonium chloride. The compounds according to the invention thus represent a valuable enrichment of the art.

If 3-amino-2,5,6-trichlorobenzoic acid ethyl ester and methyl 2-ethoxy-1-methylcarbonyl-vinyl ketone are used as starting materials, the course of the reaction can be represented by the following equation:

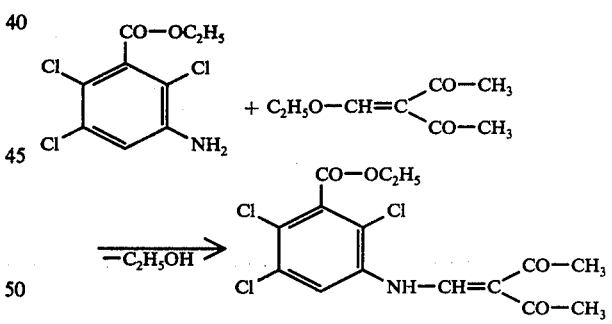

The chlorine-substituted 3-aminobenzoic acid derivatives of the formula (II) which can be used according to the invention are already known or can be prepared in accordance with generally customary processes [see R. Schröter and F. Möller, Houben-Weyl-Müller, "Methoden der organischen Chemie" ("Methods of Organic Chemistry"), volume 11/1, Thieme Verlag, Stuttgart (1957), pages 341–731].

The following may be mentioned as examples of the compounds of the formula (II) which can be used according to the invention: 3-amino-2-chlorobenzoic acid, 3-amino-2-chlorobenzoic acid methyl ester, 3-amino-2-chlorobenzoic acid ethyl ester, 3-amino-2-chlorobenzoic acid n-propyl ester, 3-amino-2-chlorobenzoic acid isopropyl ester, 3-amino-2-chloro-N-methylbenzoic acid amide, 3-amino-2-chloro-N-ethyl-benzoic acid amide, 3-amino-2,5-dichlorobenzoic acid, 3-amino-2,5-dichlorobenzoic acid methyl ester, 3-amino-2,5-dichlorobenzoic acid ethyl ester, 3-amino-2,5-dichlorobenzoic acid n-propyl ester, 3-amino-2,5-dichlorobenzoic acid isopropyl ester, 3-amino-2,5-dichloro-N-methyl-benzoic acid amide, 3-amino-2,5-dichloro-N-ethyl-benzoic acid amide, 3-amino-2,5,6-trichlorobenzoic acid, 3-amino-2,5,6-trichlorobenzoic acid methyl ester, 3-amino-2,5,6-trichlorobenzoic acid ethyl ester, 3-amino-2,5,6-trichlorobenzoic acid n-propyl ester, 3-amino-2,5,6-trichlorobenzoic acid isopropyl ester, 3-amino-2,5,6-trichloro-N-methyl-benzoic acid amide, 3-amino-2,5,6-trichloro-N-ethyl-benzoic acid amide, 3-amino-5-chlorobenzoic acid, 3-amino-5-chlorobenzoic acid methyl ester, 3-amino-5-chlorobenzoic acid ethyl ester, 3-amino-5-chlorobenzoic acid n-propyl ester, 3-amino-5-chlorobenzoic acid isopropyl ester, 3-amino-5-chloro-N-methyl-benzoic acid amide, 3-amino-5-chloro-N-ethyl-benzoic acid amide, 3-amino-5,6-dichlorobenzoic acid, 3-amino-5,6-dichlorobenzoic acid methyl ester, 3-amino-5,6-dichlorobenzoic acid ethyl ester, 3-amino-5,6-dichlorobenzoic acid n-propyl ester, 3-amino-5,6-dichlorobenzoic acid isopropyl ester, 3-amino-5,6-dichloro-N-methyl-benzoic acid amide, 3-amino-5,6-dichloro-N-ethyl-benzoic acid amide, 3-amino-6-chlorobenzoic acid, 3-amino-6-chlorobenzoic acid methyl ester, 3-amino-6-chlorobenzoic acid ethyl ester, 3-amino-6-chlorobenzoic acid n-propyl ester, 3-amino-6-chloro-N-methyl-benzoic acid amide, 3-amino-6-chloro-N-ethyl-benzoic acid amide and 3-amino-6-chlorobenzoic acid isopropyl ester.

The compounds of the formula (III) which can be used according to the invention are known and can be prepared in accordance with generally customary methods, in most cases also on an industrial scale (see L. Claisen "Liebigs Annalen der Chemie" 297, 1 (1897); Houben-Weyl "Methoden der organischen Chemie" (Methods of Organic Chemistry"), volume VIII, 623, G. Thieme Verlag, Stuttgart 1952; Beilstein 854; I, 431 and II, 899).

The following may be mentioned as individual examples of the compounds of the formula (III) which can be used according to the invention: 2-methylcarbonyl-3-methoxy-acrylic acid methyl ester, 2-methylcarbonyl-3-methoxy-acrylic acid ethyl ester, 2-methylcarbonyl-3-methoxy-acrylic acid n-propyl ester, 2-methylcarbonyl-3-methoxy-acrylic acid isopropyl ester, 2-methylcarbonyl-3-ethoxy-acrylic acid methyl ester, 2-methylcarbonyl-3-ethoxy-acrylic acid ethyl ester, 2-methylcarbonyl-3-ethoxy-acrylic acid n-propyl ester, 2-methylcarbonyl-3-ethoxy-acrylic acid isopropyl ester, 2-ethylcarbonyl-3-methoxy-acrylic acid methyl ester, 2-ethylcarbonyl-3-methoxy-acrylic acid ethyl ester, 2-ethylcarbonyl-3-methoxy-acrylic acid n-propyl ester, 2-ethylcarbonyl-3-methoxy-acrylic acid isopropyl ester, 2-ethylcarbonyl-3-ethoxy-acrylic acid methyl ester, 2-ethylcarbonyl-3-ethoxy-acrylic acid ethyl ester, 2-ethylcarbonyl-3-ethoxy-acrylic acid n-propyl ester, 2-ethylcarbonyl-3-ethoxy-acrylic acid isopropyl ester, 2-n-propylcarbonyl-3-methoxy-acrylic acid methyl ester, 2-n-propylcarbonyl-3-methoxy-acrylic acid ethyl ester, 2-n-propylcarbonyl-3-methoxy-acrylic acid n-propyl ester, 2-n-propylcarbonyl-3-ethoxy-acrylic acid isopropyl ester, 2-n-propylcarbonyl-3-ethoxy-acrylic acid methyl ester, 2-n-propylcarbonyl-3-ethoxy-acrylic acid ethyl ester, 2-n-propylcarbonyl-3-ethoxy-acrylic acid n-propyl ester, 2-n-propylcarbonyl-3-ethoxy-acrylic acid isopropyl ester, 2-iso-propylcarbonyl-3-methoxy-acrylic acid methyl ester, 2-iso-propylcarbonyl-3-methoxy-acrylic acid ethyl ester, 2-iso-propylcarbonyl-3-methoxy-acrylic acid n-propyl ester, 2-iso-propylcarbonyl-3-methoxy-acrylic acid isopropyl ester, 2-iso-propylcarbonyl-3-ethoxy-acrylic acid methyl ester, 2-iso-propylcarbonyl-3-ethoxy-acrylic acid ethyl ester, 2-iso-propylcarbonyl-3-ethoxy-acrylic acid n-propyl ester, 2-iso-propylcarbonyl-3-ethoxy-acrylic acid isopropyl ester, 2-cyano-3-methoxy-acrylic acid methyl ester, 2-cyano-3-methoxy-acrylic acid ethyl ester, 2-cyano-3-methoxy-acrylic acid n-propyl ester, 2-cyano-3-methoxy-acrylic acid isopropyl ester, 2-cyano-3-ethoxy-acrylic acid methyl ester, 2-cyano-3-ethoxy-acrylic acid ethyl ester, 2-cyano-3-ethoxy-acrylic acid n-propyl ester, 2-cyano-3-ethoxy-acrylic acid isopropyl ester, 2-carbomethoxy-3-methoxy-acrylic acid methyl ester, 2-carbomethoxy-3-ethoxy-acrylic acid methyl ester, 2-carbethoxy-3-methoxy-acrylic acid ethyl ester, 2-carbethoxy-3-ethoxy-acrylic acid ethyl ester, 2-carbo-n-propoxy-3-methoxy-acrylic acid n-propyl ester, 2carbo-n-propoxy-3-ethoxy-acrylic acid n-propyl ester, 2-carb-iso-propoxy-3-methoxy-acrylic acid isopropyl ester, 2-carb-isopropoxy-3-ethoxy-acrylic acid isopropyl ester, methyl 1-methylcarbonyl-2-methoxy-vinyl ketone, ethyl 1-ethylcarbonyl-2-methoxy-vinyl ketone, methyl 1-methylcarbonyl-2-ethoxy-vinyl ketone and ethyl 1-ethylcarbonyl-2-ethoxy-vinyl ketone.

The process according to the invention for the preparation of the new chlorine-substituted vinylaminobenzoic acid derivatives of the formula (I) is preferably carried out in the presence of a suitable solvent or diluent. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, such as diethyl ether, dibutyl ether, dioxan and tetrahydrofuran; ketones, for example acetone, methyl ethyl ketone, methyl isopropyl ketone and methyl isobutyl ketone; furthermore nitriles, such as acetonitrile and propionitrile; and alcohols such as, for example, ethanol.

The reaction temperatures can be varied within a fairly wide range. In general, the reaction is carried out at between 10° and 150° C, preferably between 20° and 120° C.

The reaction according to the invention is in general carried out under normal pressure.

In carrying out the process according to the invention for the preparation of the compounds of the formula (I), 1 to 4 moles of a compound of the formula (III) are generally employed per mole of an aminobenzoic acid derivative of the formula (II).

In general, the reaction products of the formula (I) are isolated by filtering off, after the end of the reaction, the precipitate which has been produced, washing it with an organic solvent, and recrystallising and drying it. In some cases a precipitate does not separate out. In that case the procedure followed is that after the reaction has ended the reaction solution is cooled and an organic solvent is added, whereupon a precipitate forms. The latter is filtered off, washed, recrystallised and dried.

The compounds of the formula (I) which can be prepared in accordance with the invention are obtained, after working up, in a crystalline form; they can in most cases be characterised as pure substances by their sharp melting point.

The following may be mentioned as individual examples of the chlorine-substituted vinylaminobenzoic acid derivatives of the formula (I), according to the invention: 2-chloro-3-[2,2-bis-(carbomethoxy)-vinylamino]-benzoic acid, 2-chloro-3-[2,2-bis-(carbomethoxy)-vinylamino]-benzoic acid methyl ester, 2-chloro-3-[2,2-bis-(carbomethoxy)-vinylamino]-benzoic acid ethyl ester, 2-chloro-3-[2,2-bis-(carbomethoxy)-vinylamino]-benzoic acid n-propyl ester, 2-chloro-3-[2,2-bis-(carbomethoxy)-vinylamino]-benzoic acid isopropyl ester, 2-chloro-3-[2,2-bis-(carbomethoxy)-vinylamino]-N-methyl-benzoic acid amide, 2-chloro-3-[2,2-bis-(carbomethoxy)-vinylamino]-N-ethyl-benzoic acid amide, 2-chloro-3-[2,2-bis-(carbethoxy)-vinylamino]-benzoic acid, 2-chloro-3-[2,2-bis-(carbethoxy)-vinylamino]-benzoic acid methyl ester, 2-chloro-3-[2,2-bis-(carbethoxy)-vinylamino]-benzoic acid ethyl ester, 2-chloro-3-[2,2-bis-(carbethoxy)-vinylamino]-benzoic acid n-propyl ester, 2-chloro-3-[2,2-bis-(carbethoxy)-vinylamino]-benzoic acid isopropyl ester, 2-chloro-3-[2,2-bis-(carbethoxy)-vinylamino]-N-methyl-benzoic acid amide, 2-chloro-3-[2,2-bis-(carbethoxy)-vinylamino]-N-ethyl-benzoic acid amide, 2-chloro-3-[2,2-bis-(carbo-n-propoxy)-vinylamino]-benzoic acid, 2-chloro-3-[2,2-bis-(carbo-n-propoxy)-vinylamino]-benzoic acid methyl ester, 2-chloro-3-[2,2-bis-(carbo-n-propoxy)-vinylamino]-benzoic acid ethyl ester, 2-chloro-3-[2,2-bis-(carbo-n-propoxy)-vinylamino]-benzoic acid n-propyl ester, 2-chloro-3-[2,2-bis-(carbo-n-propoxy)-vinylamino]-benzoic acid isopropyl ester, 2-chloro-3-[2,2-bis-(carbo-n-propoxy)-vinylamino]-N-methyl-benzoic acid amide, 2-chloro-3-[2,2-bis-(carbo-n-propoxy)-vinylamino]-N-ethyl-benzoic acid amide, 2-chloro-3-[2,2-bis-(carb-isopropoxy)-vinylamino]-benzoic acid, 2-chloro-3-[2,2-bis-(carb-isopropoxy)-vinylamino]-benzoic acid methyl ester, 2-chloro-3-[2,2-bis-(carb-isopropoxy)-vinylamino]-benzoic acid ethyl ester, 2-chloro-3-[2,2-bis-(carb-isopropoxy)-vinylamino]-benzoic acid n-propyl ester, 2-chloro-3-[2,2-bis-(carb-isopropoxy)-vinylamino]-benzoic acid isopropyl ester, 2-chloro-3-[2,2-bis-(carb-isopropoxy)-vinylamino]-N-methyl-benzoic acid amide, 2-chloro-3-[2,2-bis-(carb-isopropoxy)-vinylamino]-N-ethyl-benzoic acid amide, 2-chloro-3-[2,2-bis-(methylcarbonyl)-vinylamino]-benzoic acid, 2-chloro-3-[2,2-bis-(methylcarbonyl)-vinylamino]-benzoic acid methyl ester, 2-chloro-3-[2,2-bis-(methylcarbonyl)-vinylamino]-benzoic acid ethyl ester, 2-chloro-3-[2,2-bis-(methylcarbonyl)-vinylamino]-benzoic acid n-propyl ester, 2-chloro-3-[2,2-bis-(methylcarbonyl)-vinylamino]-benzoic acid isopropyl ester, 2-chloro-3-[2,2-bis-(methylcarbonyl)-vinylamino]-N-methyl-benzoic acid amide, 2-chloro-3-[2,2-bis-(methylcarbonyl)-vinylamino]-N-ethyl-benzoic acid amide, 2-chloro-3-[2,2-bis-(ethylcarbonyl)-vinylamino]-benzoic acid, 2-chloro-3-[2,2-bis-(ethylcarbonyl)-vinylamino]-benzoic acid methyl ester, 2-chloro-3-[2,2-bis-(ethylcarbonyl)-vinylamino]-benzoic acid ethyl ester, 2-chloro-3-[2,2-bis-(ethylcarbonyl)-vinylamino]-benzoic acid n-propyl ester, 2-chloro-3-[2,2-bis-(ethylcarbonyl)-vinylamino]-benzoic acid isopropyl ester, 2-chloro-3-[2,2-bis-(ethylcarbonyl)-vinylamino]-N-methyl-benzoic acid amide, 2-chloro-3-[2,2-bis-(ethylcarbonyl)-vinylamino]-N-ethyl-benzoic acid amide, 2-chloro-3-[2,2-bis-(n-propylcarbonyl)-vinylamino]-benzoic acid, 2-chloro-3-[2,2-bis-(n-propylcarbonyl)-vinylamino]-benzoic acid methyl ester, 2-chloro-3-[2,2-bis-(n-propylcarbonyl)-vinylamino]-benzoic acid ethyl ester, 2-chloro-3-[2,2-bis-(n-propylcarbonyl)-vinylamino]-benzoic acid n-propyl ester, 2-chloro-3-[2,2-bis-(n-propylcarbonyl)-vinylamino]-benzoic acid isopropyl ester, 2-chloro-3-[2,2-bis-(n-propylcarbonyl)-vinylamino]-N-methyl-benzoic acid amide, 2-chloro-3-[2,2-bis-(n-propylcarbonyl)-vinylamino]-N-ethyl-benzoic acid amide, 2-chloro-3-[2,2-bis-(iso-propylcarbonyl)-vinylamino]-benzoic acid, 2-chloro-3-[2,2-bis-(iso-propylcarbonyl)-vinylamino]-benzoic acid methyl ester, 2-chloro-3-[2,2-bis-(iso-propylcarbonyl)-vinylamino]-benzoic acid ethyl ester, 2-chloro-3-[2,2-bis-(iso-propylcarbonyl)-vinylamino]-benzoic acid n-propyl ester, 2-chloro-3-[2,2-bis-(iso-propylcarbonyl)-vinylamino]-benzoic acid isopropyl ester, 2-chloro-3-[2,2-bis-(iso-propylcarbonyl)-vinylamino]-N-methyl-benzoic acid amide, 2-chloro-3-[2,2-bis-(iso-propylcarbonyl)-vinylamino]-N-ethyl-benzoic acid amide, 2-chloro-3-[(2-carbomethoxy-2-methylcarbonyl)-vinylamino]-benzoic acid, 2-chloro-3-[(2-carbomethoxy-2-methylcarbonyl)-vinylamino]-benzoic acid methyl ester, 2-chloro-3-[(2-carbomethoxy-2-methylcarbonyl)-vinylamino]-benzoic acid ethyl ester, 2-chloro-3-[(2-carbomethoxy-2-methylcarbonyl)-vinylamino]-benzoic acid n-propyl ester, 2-chloro-3-[(2-carbomethoxy-2-methylcarbonyl)-vinylamino]-benzoic acid isopropyl ester, 2-chloro-3-[(2-carbomethoxy-2-methylcarbonyl)-vinylamino]-N-methyl-benzoic acid amide, 2-chloro-3-[(2-carbomethoxy-2-methylcarbonyl)-vinylamino]-N-ethyl-benzoic acid amide, 2-chloro-3-[(2-carbethoxy-2-methylcarbonyl)-vinylamino]-benzoic acid, 2-chloro-3-[(2-carbethoxy-2-methylcarbonyl)-vinylamino]-benzoic acid methyl ester, 2-chloro-3-[(2-carbethoxy-2-methylcarbonyl)-vinylamino]-benzoic acid ethyl ester, 2-chloro-3-[(2-carbethoxy-2-methylcarbonyl)-vinylamino]-benzoic acid n-propyl ester, 2-chloro-3-[(2-carbethoxy-2-methylcarbonyl)-vinylamino]-benzoic acid isopropyl ester, 2-chloro-3-[(2-carbethoxy-2-methylcarbonyl)-vinylamino]-N-methyl-benzoic acid amide, 2-chloro-3-[(2-carbethoxy-2-methylcarbonyl)-vinylamino]-N-[(2-carbethoxy-2-methylcarbonyl)-vinylamino]-N-ethyl-benzoic acid amide, 2-chloro-3-[(2-carbo-n-propoxy-2-methylcarbonyl)-vinylamino]-benzoic acid, 2-chloro-3-[(2-carbo-n-propoxy-2-methylcarbonyl)-vinylamino]-benzoic acid methyl ester, 2-chloro-3-[(2-carbo-n-propoxy-2-methylcarbonyl)-vinylamino]-benzoic acid ethyl ester, 2-chloro-3-[(2-carbo-n-propoxy-2-methylcarbonyl)-vinylamino]-benzoic acid n-propyl ester, 2-chloro-3-[(2-carbo-n-propoxy-2-methylcarbonyl)-vinylamino]-benzoic acid isopropyl ester, 2-chloro-3-[(2-carbo-n-propoxy-2-methylcarbonyl)-vinylamino]-N-methyl-benzoic acid amide, 2-chloro-3-[(2-carbo-n-propoxy-2-methylcarbonyl)-vinylamino]-N-ethyl-benzoic acid amide, 2-chloro-3-[(2-carb-isopropoxy-2-methylcarbonyl)-vinylamino]-benzoic acid, 2-chloro-3-[(2-carb-isopropoxy-2-methylcarbonyl)-vinylamino]-benzoic acid methyl ester, 2-chloro-3-[(2-carb-isopropoxy-2-methylcarbonyl)-vinylamino]-benzoic acid ethyl ester, 2-chloro-3-[(2-carb-isopropoxy-2-methylcarbonyl)-vinylamino]-benzoic acid n-propyl ester, 2-chloro-3-[(2-carb-isopropoxy-2-methylcarbonyl)-vinylamino]-benzoic acid isopropyl ester, 2-chloro-3-[(2-carb-isopropoxy-2-methylcarbonyl)-vinylamino]-N-methyl-benzoic acid amide, 2-chloro-3-[(2-carb-isopropoxy-2-methylcarbonyl)-vinylamino]-N-ethyl-benzoic acid amide, 2-chloro-3-[(2-carbomethoxy-2-cyano)-vinylamino]-benzoic acid, 2-chloro-3-[(2-carbomethoxy-2-cyano)-vinylamino]-benzoic acid methyl ester, 2-chloro-3-[(2-carbomethoxy-2-cyano)-vinylamino]-benzoic acid ethyl ester, 2-chloro-3-[(2- carbomethoxy-2-cyano)-vinylamino]-benzoic acid n-propyl ester, 2-chloro-3-[(2-carbomethoxy-2-cyano)-vinylamino]-benzoic acid isopropyl ester, 2-chloro-3-[(2-carbomethoxy-2-cyano)-vinylamino]-N-methyl-benzoic acid amide, 2-chloro-3-[(2-carbomethoxy-2-cyano)-vinylamino]-N-ethyl-benzoic acid amide, 2-chloro-3-[(2-carbethoxy-2-cyano)-vinylamino]-benzoic acid, 2-chloro-3-[(2-carbethoxy-2-cyano)-vinylamino]-benzoic acid methyl ester, 2-chloro-3-[(2-carbethoxy-2-cyano)-vinylamino]-benzoic acid ethyl ester, 2-chloro-3-[(2-carbethoxy-2-cyano)-vinylamino]-benzoic acid n-propyl ester, 2-chloro-3-[(2-carbethoxy-2-cyano)-vinylamino]-benzoic acid isopropyl ester, 2-chloro-3-[(2-carbethoxy-2-cyano)-vinylamino]-N-methyl-benzoic acid amide, 2-chloro-3-[(2-carbethoxy-2-cyano)-vinylamino]-N-ethyl-benzoic acid amide, 2-chloro-3-[(2-carbo-n-propoxy-2-cyano)-vinylamino]-benzoic acid, 2-chloro-3-[(2-carbo-n-propoxy-2-cyano)-vinylamino]-benzoic acid methyl ester, 2-chloro-3-[(2-carbo-n-propoxy-2-cyano)-vinylamino]-benzoic acid ethyl ester, 2-chloro-3-[(2-carbo-n-propoxy-2-cyano)-vinylamino]-benzoic acid n-propyl ester, 2-chloro-3-[(2-carbo-n-propoxy-2-cyano)-vinylamino]-benzoic acid isopropyl ester, 2-chloro-3-[(2-carbo-n-propoxy-2-cyano)-vinylamino]-N-methyl-benzoic acid amide, 2-chloro-3-[(2-carbo-n-propoxy-2-cyano)-vinylamino]-N-ethyl-benzoic acid amide, 2-chloro-3-[(2-carb-isopropoxy-2-cyano)-vinylamino]-benzoic acid, 2-chloro-3-[(2-carb-isopropoxy-2-cyano)-vinyl-amino]-benzoic acid methyl ester, 2-chloro-3-[(2-carb-iso-propoxy-2-cyano)-vinylamino]-benzoic acid ethyl ester, 2-chloro-3-[(2-carb-isopropoxy-2-cyano)-vinylamino]-benzoic acid n-propyl ester, 2-chloro-3-[(2-carb-isopropoxy-2-cyano)-vinylamino]-benzoic acid isopropyl ester, 2-chloro-3-[(2-carb-isopropoxy-2-cyano)-vinylamino]-N-methyl-benzoic acid amide, 2-chloro-3-[(2-carb-isopropoxy-2-cyano)-vinylamino]-N-ethyl-benzoic acid amide, 2,5-dichloro-3-[(2-carbomethoxy-2-methylcarbonyl)-vinylamino]-benzoic acid, 2,5-dichloro-3-[(2-carbomethoxy-2-methylcarbonyl)-vinylamino]-benzoic acid methyl ester, 2,5-dichloro-3-[(2-carbomethoxy-2-methylcarbonyl)-vinylamino]-benzoic acid ethyl ester, 2,5-dichloro-3-[(2-carbomethoxy-2-methylcarbonyl)-vinylamino]-benzoic acid n-propyl ester, 2,5-dichloro-3-[(2-carbomethoxy-2-methylcarbonyl)-vinylamino]-benzoic acid isopropyl ester, 2,5-dichloro-3-[(2-carbomethoxy-2-methylcarbonyl)-vinylamino]-N-methyl-benzoic acid amide, 2,5-dichloro-3-[(2-carbomethoxy-2-methylcarbonyl)-vinylamino]-N-ethyl-benzoic acid amide, 2,5-dichloro-3-[(2-carbethoxy-2-methylcarbonyl)-vinylamino]-benzoic acid, 2,5-dichloro-3-[(2-carbethoxy-2-methylcarbonyl)-vinylamino]-benzoic acid methyl ester, 2,5-dichloro-3-[(2-carbethoxy-2-methylcarbonyl)-vinylamino]-benzoic acid ethyl ester, 2,5-dichloro-3-[(2-carbethoxy-2-methylcarbonyl)-vinylamino]-benzoic acid n-propyl ester, 2,5-dichloro-3-[(2-carbethoxy-2-methylcarbonyl)-vinylamino]-benzoic acid isopropyl ester, 2,5-dichloro-3-[(2-carbethoxy-2-methylcarbonyl)-vinylamino]-N-methyl-benzoic acid amide, 2,5-dichloro-3-[(2-carbethoxy-2-methylcarbonyl)-vinylamino]-N-ethyl-benzoic acid amide, 2,5-dichloro-3-[(2-carbo-n-propoxy-2-methylcarbonyl)-vinylamino]-benzoic acid, 2,5-dichloro-3-[(2-carbo-n-propoxy-2-methylcarbonyl)-vinylamino]-benzoic acid methyl ester, 2,5-dichloro-3-[(2-carbo-n-propoxy-2-methylcarbonyl)-vinylamino]-benzoic acid ethyl ester, 2,5-dichloro-3-[(2-carbo-n-propoxy-2-methylcarbonyl)-vinylamino]-benzoic acid n-propyl ester, 2,5-dichloro-3-[(2-carbo-n-propoxy-2-methylcarbonyl)-vinylamino]-benzoic acid isopropyl ester, 2,5-dichloro-3-[(2-carbo-n-propoxy-2-methylcarbonyl)-vinylamino]-N-methyl-benzoic acid amide, 2,5-dichloro-3-[(2-carbo-n-propoxy-2-methylcarbonyl)-vinylamino]-N-ethyl-benzoic acid amide, 2,5-dichloro-3-[(2-carb-isopropoxy-2-methylcarbonyl)-vinylamino]-benzoic acid, 2,5-dichloro-3-[(2-carb-isopropoxy-2-methylcarbonyl)-vinylamino]-benzoic acid methyl ester, 2,5-dichloro-3-[(2-carb-isopropoxy-2-methylcarbonyl)-vinylamino]-benzoic acid ethyl ester, 2,5-dichloro-3-[(2-carb-isopropoxy-2-methylcarbonyl)-vinylamino]-benzoic acid n-propyl ester, 2,5-dichloro-3-[(2-carb-isopropoxy-2-methylcarbonyl)-vinylamino]-benzoic acid isopropyl ester, 2,5-dichloro-3-[(2-carb-isopropoxy-2-methylcarbonyl)-vinylamino]-N-methyl-benzoic acid amide, 2,5-dichloro-3-[(2-carb-isopropoxy-2-methylcarbonyl)-vinylamino]-N-ethyl-benzoic acid amide, 2,5-dichloro-3-[(2-carbomethoxy-2-cyano)-vinylamino]-benzoic acid, 2,5-dichloro-3-[(2-carbomethoxy-2-cyano)-vinylamino]-benzoic acid methyl ester, 2,5-dichloro-3-[(2-carbomethoxy-2-cyano)-vinylamino]-benzoic acid ethyl ester, 2,5-dichloro-3-[(2-carbomethoxy-2-cyano)-vinylamino]-benzoic acid n-propyl ester, 2,5-dichloro-3-[(2-carbomethoxy-2-cyano)-vinylamino]-benzoic acid isopropyl ester, 2,5-dichloro-3-[(2-carbomethoxy-2-cyano)-vinylamino]-N-methyl-benzoic acid amide, 2,5-dichloro-3-[(2-carbomethoxy-2-cyano)-vinylamino]-N-ethyl-benzoic acid amide, 2,5-dichloro-3-[(2-carbethoxy-2-cyano)-vinylamino]-benzoic acid, 2,5-dichloro-3-[(2-carbethoxy-2-cyano)-vinylamino]-benzoic acid methyl ester, 2,5-dichloro-3-[(2-carbethoxy-2-cyano)-vinylamino]-benzoic acid ethyl ester, 2,5-dichloro-3-[(2-carbethoxy-2-cyano)-vinylamino]-benzoic acid n-propyl ester, 2,5-dichloro-3-[(2-carbethoxy-2-cyano)-vinylamino]-benzoic acid isopropyl ester, 2,5-dichloro-3-[(2-carbethoxy-2-cyano)-vinylamino]-N-methyl-benzoic acid amide, 2,5-dichloro-3-[(2-carbethoxy-2-cyano)-vinylamino]-N-ethyl-benzoic acid amide, 2,5-dichloro-3-[(2-carbo-n-propoxy-2-cyano)-vinylamino]-benzoic acid, 2,5-dichloro-3-[(2-carbo-n-propoxy-2-cyano)-vinyl-amino]-benzoic acid methyl ester, 2,5-dichloro-3-[(2-carbo-n-propoxy-2-cyano)-vinylamino]-benzoic acid ethyl ester, 2,5-dichloro-3-[(2-carbo-n-propoxy-2-cyano)-vinylamino]-benzoic acid n-propyl ester, 2,5-dichloro-3-[(2-carbo-n-propoxy-2-cyano)-vinylamino]-benzoic acid isopropyl ester, 2,5-dichloro-3-[(2-carbo-n-propoxy-2-cyano)-vinylamino]-N-methyl-benzoic acid amide, 2,5-dichloro-3-[(2-carbo-n-propoxy-2-cyano)-vinylamino]-N-ethyl-benzoic acid amide, 2,5-dichloro-3-[(2-carb-isopropoxy-2-cyano)-vinylamino]-benzoic acid, 2,5-dichloro-3-[(2-carb-isopropoxy-2-cyano)-vinylamino]-benzoic acid methyl ester, 2,5-dichloro-3-[(2-carb-isopropoxy-2-cyano)-vinyl-amino]-benzoic acid ethyl ester, 2,5-dichloro-3-[(2-carb-isopropoxy-2-cyano)-vinylamino]-benzoic acid n-propyl ester, 2,5-dichloro-3-[(2-carb-isopropoxy-2-cyano)-vinylamino]-benzoic acid isopropyl ester, 2,5-dichloro-3-[(2-carb-isopropoxy-2-cyano)-vinylamino]-N-methyl-benzoic acid amide, 2,5-dichloro-3-[(2-carb-isopropoxy-2-cyano)-vinylamino]-N-ethyl-benzoic acid amide, 2,6-dichloro-3-[(2-carbomethoxy-2-methylcarbonyl)-vinylamino]-benzoic acid 2,6-dichloro-3-[(2-carbomethoxy-2-methylcarbonyl)-vinylamino]-benzoic acid methyl ester, 2,6-dichloro-3-[(2-carbomethoxy-2-methylcarbonyl)-vinylamino]-benzoic acid ethyl ester, 2,6-dichloro-3-[(2-carbomethoxy-2-methylcarbonyl)-vinylamino]-benzoic acid n-propyl ester, 2,6-dichloro-3-

[(2-carbomethoxy-2-methylcarbonyl)-vinylamino]-benzoic acid isopropyl ester, 2,6-dichloro-3-[(2-carbomethoxy-2-methylcarbonyl)-vinylamino]-N-methyl-benzoic acid amide, 2,6-dichloro-3-[(2-carbomethoxy-2-methylcarbonyl)-vinylamino]-N-ethyl-benzoic acid amide, 2,6-dichloro-3-[(2-carbethoxy-2-methylcarbonyl)-vinylamino]-benzoic acid, 2,6-dichloro-3-[(2-carbethoxy-2-methylcarbonyl-vinylamino]-benzoic acid methyl ester, 2,6-dichloro-3-[(2-carbethoxy-2-methylcarbonyl)-vinylamino]-benzoic acid ethyl ester, 2,6-dichloro-3-[(2-carbethoxy-2-methylcarbonyl)-vinylamino]-benzoic acid n-propyl ester, 2,6-dichloro-3-[(2-carbethoxy-2-methylcarbonyl)-vinylamino]-benzoic acid isopropyl ester, 2,6-dichloro-3-[(2-carbethoxy-2-methylcarbonyl)-vinylamino]-N-methyl-benzoic acid amide, 2,6-dichloro-3-[(2-carbethoxy-2-methylcarbonyl)-vinylamino]-N-ethyl-benzoic acid amide, 2,6-dichloro-3-[(2-carbo-n-propoxy-2-methylcarbonyl)-vinylamino]-benzoic acid, 2,6-dichloro-3-[(2-carbo-n-propoxy-2-methylcarbonyl)-vinylamino]-benzoic acid methyl ester, 2,6-dichloro-3-[(2-carbo-n-propoxy-2-methylcarbonyl)-vinylamino]-benzoic acid ethyl ester, 2,6-dichloro-3-[(2-carbo-n-propoxy-2-methylcarbonyl)-vinylamino]-benzoic acid n-propyl ester, 2,6-dichloro-3-[(2-carbo-n-propoxy-2-methylcarbonyl)-vinylamino]-benzoic acid isopropyl ester, 2,6-dichloro-3-[(2-carbo-n-propoxy-2-methylcarbonyl)-vinylamino]-N-methyl-benzoic acid amide, 2,6-dichloro-3-[(2-carbo-n-propoxy-2-methylcarbonyl)-vinylamino]-N-ethyl-benzoic acid amide, 2,6-dichloro-3-[(2-carb-isopropoxy-2-methylcarbonyl)-vinylamino]-benzoic acid, 2,6-dichloro-3-[(2-carb-isopropoxy-2-methylcarbonyl)-vinylamino]-benzoic acid methyl ester, 2,6-dichloro-3-[(2-carb-isopropoxy-2-methylcarbonyl)-vinylamino]-benzoic acid ethyl ester, 2,6-dichloro-3-[(2-carb-isopropoxy-2-methylcarbonyl)-vinylamino]-benzoic acid n-propyl ester, 2,6-dichloro-3-[(2-carb-isopropoxy-2-methylcarbonyl)-vinylamino]-benzoic acid isopropyl ester, 2,6-dichloro-3-[(2-carb-isopropoxy-2-methylcarbonyl)-vinylamino]-N-methyl-benzoic acid amide, 2,6-dichloro-3-[(2-carb-isopropoxy-2-methylcarbonyl)-vinylamino]-N-ethyl-benzoic acid amide, 2,6-dichloro-3-[(2-carbomethoxy-2-cyano)-vinylamino]-benzoic acid, 2,6-dichloro-3-[(2-carbomethoxy-2-cyano)-vinylamino]-benzoic acid methyl ester, 2,6-dichloro-3-[(2-carbomethoxy-2-cyano)-vinylamino]-benzoic acid ethyl ester, 2,6-dichloro-3-[(2-carbomethoxy-2-cyano)-vinyl-amino]-benzoic acid n-propyl ester, 2,6-dichloro-3-[(2-carbomethoxy-2-cyano)-vinylamino]-benzoic acid isopropyl ester, 2,6-dichloro-3-[(2-carbomethoxy-2-cyano)-vinylamino]-N-methyl-benzoic acid amide, 2,6-dichloro-3-[(2-carbomethoxy-2-cyano)-vinylamino]-N-ethyl-benzoic acid amide, 2,6-dichloro-3-[(2-carbethoxy-2-cyano)-vinylamino]-benzoic acid, 2,6-dichloro-3-[(2-carbethoxy-2-cyano)-vinylamino]-benzoic acid methyl ester, 2,6-dichloro-3-[(2-carbethoxy-2-cyano)-vinylamino]-benzoic acid ethyl ester, 2,6-dichloro-3-[(2-carbethoxy-2-cyano)-vinylamino]-benzoic acid n-propyl ester, 2,6-dichloro-3-[(2-carbethoxy-2-cyano)-vinylamino]-benzoic acid isopropyl ester, 2,6-dichloro-3-[(2-carbethoxy-2-cyano)-vinylamino]-N-methyl-benzoic acid amide, 2,6-dichloro-3-[(2-carbethoxy-2-cyano)-vinylamino]-N-ethyl-benzoic acid amide, 2,6-dichloro-3-[(2-carbo-n-propoxy-2-cyano)-vinylamino]-benzoic acid, 2,6-dichloro-3-[(2-carbo-n-propoxy-2-cyano)-vinylamino]-benzoic acid methyl ester, 2,6-dichloro-3-[(2-carbo-n-propoxy-2-cyano)-vinylamino]-benzoic acid ethyl ester, 2,6-dichloro-3-[(2-carbo-n-propoxy-2-cyano)-vinylamino]-benzoic acid n-propyl ester, 2,6-dichloro-3-[(2-carbo-n-propoxy-2-cyano)-vinylamino]-benzoic acid isopropyl ester, 2,6-dichloro-3-[(2-carbo-n-propoxy-2-cyano)-vinylamino]-N-methyl-benzoic acid amide, 2,6-dichloro-3-[(2-carbo-n-propoxy-2-cyano)-vinylamino]-N-ethyl-benzoic acid amide, 2,6-dichloro-3-[(2-carb-isopropoxy-2-cyano)-vinylamino]-benzoic acid, 2,6-dichloro-3-[(2-carb-isopropoxy-2-cyano)-vinylamino]-benzoic acid methyl ester, 2,6-dichloro-3-[(2-carb-isopropoxy-2-cyano)-vinylamino]-benzoic acid ethyl ester, 2,6-dichloro-3-[(2-carb-isopropoxy-2-cyano)-vinylamino]-benzoic acid n-propyl ester, 2,6-dichloro-3-[(2-carb-isopropoxy-2-cyano)-vinylamino]-benzoic acid isopropyl ester, 2,6-dichloro-3-[(2-carb-isopropoxy-2-cyano)-vinylamino]-N-methyl-benzoic acid amide, 2,6-dichloro-3-[(2-carb-isopropoxy-2-cyano)-vinylamino]-N-ethyl-benzoic acid amide, 2,5,6-trichloro-3-[(2-carbomethoxy-2-methylcarbonyl)-vinylamino]-benzoic acid, 2,5,6-trichloro-3-[(2-carbomethoxy-2-methylcarbonyl)-vinylamino]-benzoic acid methyl ester, 2,5,6-trichloro-3-[(2-carbomethoxy-2-methylcarbonyl)-vinylamino]-benzoic acid ethyl ester, 2,5,6-trichloro-3-[(2-carbomethoxy-2-methylcarbonyl)-vinylamino]-benzoic acid n-propyl ester, 2,5,6-trichloro-3-[(2-carbomethoxy-2-methylcarbonyl)-vinylamino]-benzoic acid isopropyl ester, 2,5,6-trichloro-3-[(2-carbomethoxy-2-methylcarbonyl)-vinylamino]-N-methyl-benzoic acid amide, 2,5,6-trichloro-3-[(2-carbomethoxy-2-methylcarbonyl)-vinylamino]-N-ethyl-benzoic acid amide, 2,5,6-trichloro-3-[(2-carbethoxy-2-methylcarbonyl)-vinylamino]-benzoic acid, 2,5,6-trichloro-3-[(2-carbethoxy-2-methylcarbonyl)-vinylamino]-benzoic acid methyl ester, 2,5,6-trichloro-3-[(2-carbethoxy-2-methylcarbonyl)-vinylamino]-benzoic acid ethyl ester, 2,5,6-trichloro-3-[(2-carbethoxy-2-methylcarbonyl)-vinylamino]-benzoic acid n-propyl ester, 2,5,6-trichloro-3-[(2-carbethoxy-2-methylcarbonyl)-vinylamino]-benzoic acid isopropyl ester, 2,5,6-trichloro-3-[(2-carbethoxy-2-methylcarbonyl)-vinylamino]-N-methyl-benzoic acid amide, 2,5,6-trichloro-3-[(2-carbethoxy-2-methylcarbonyl)-vinylamino]-N-ethyl-benzoic acid amide, 2,5,6-trichloro-3-[(2-carbo-n-propoxy-2-methylcarbonyl)-vinylamino]-benzoic acid, 2,5,6-trichloro-3-[(2-carbo-n-propoxy-2-methylcarbonyl)-vinylamino]-benzoic acid methyl ester, 2,5,6-trichloro-3-[(2-carbo-n-propoxy-2-methylcarbonyl)-vinylamino]-benzoic acid ethyl ester, 2,5,6-trichloro-3-[(2-carbo-n-propoxy-2-methylcarbonyl)-vinylamino]-benzoic acid n-propyl ester, 2,5,6-trichloro-3-[(2-carbo-n-propoxy-2-methylcarbonyl)-vinylamino]-benzoic acid isopropyl ester, 2,5,6-trichloro-3-[(2-carbo-n-propoxy-2-methylcarbonyl)-vinylamino]-N-methyl-benzoic acid amide, 2,5,6-trichloro-3-[(2-carbo-n-propoxy-2-methylcarbonyl)-vinylamino]-N-ethyl-benzoic acid amide, b 2,5,6-trichloro-3-[(2-carb-isoporpoxy-2-methylcarbonyl)-vinylamino]-benzoic acid, 2,5,6-trichloro-3-[(2-carb-isopropoxy-2-methylcarbonyl)-vinylamino]-benzoic acid methyl ester, 2,5,6-trichloro-3-[(2-carb-isopropoxy-2-methylcarbonyl)-vinylamino]-benzoic acid ethyl ester, 2,5,6-trichloro-3-[(2-carb-isopropoxy-2-methylcarbonyl)-vinylamino]-benzoic acid n-propyl ester, 2,5,6-trichloro-3-[(2-carb-isopropoxy-2-methylcarbonyl)-vinylamino]-benzoic acid isopropyl ester, 2,5,6-trichloro-3-[(2-carb-isopropoxy-2-methylcarbonyl)-vinylamino]-N-methyl-benzoic acid amide, 2,5,6-trichloro-3-[(2-carb-isopropoxy-2-methylcarbonyl)- vinylamino]-N-ethyl-benzoic acid amide, 2,5,6-trichloro-3-[(2-carbomethoxy-2-cyano)-vinylamino]-benzoic acid, 2,5,6-trichloro-3-[(2-carbomethoxy-2-cyano)-vinylamino]-benzoic acid methyl ester, 2,5,6-trichloro-3-[(2-carbomethoxy-2-cyano)-vinylamino]-benzoic acid ethyl ester, 2,5,6-trichloro-3-[(2-carbomethoxy-2-cyano)-vinylamino]-benzoic acid n-propyl ester, 2,5,6-trichloro-3-[(2-carbomethoxy-2-cyano)-vinylamino]-benzoic acid isopropyl ester, 2,5,6-trichloro-3-[(2-carbomethoxy-2-cyano)-vinylamino]-N-methyl-benzoic acid amide, 2,5,6-trichloro-3-[(2-carbomethoxy-2-cyano)-vinylamino]-N-ethyl-benzoic acid amide, 2,5,6-trichloro-3-[(2-carbethoxy-2-cyano)-vinylamino]-benzoic acid, 2,5,6-trichloro-3-[(2-carbethoxy-2-cyano)-vinylamino]-benzoic acid methyl ester, 2,5,6-trichloro-3-[(2-carbethoxy-2-cyano)-vinylamino]-benzoic acid ethyl ester, 2,5,6-trichloro-3-[(2-carbethoxy-2-cyano)-vinylamino]-benzoic acid n-propyl ester, 2,5,6-trichloro-3-[(2-carbethoxy-2-cyano)-vinylamino]-benzoic acid isopropyl ester, 2,5,6-trichloro-3-[(2-carbethoxy-2-cyano)-vinylamino]-N-methyl-benzoic acid amide, 2,5,6-trichloro-3-[(2-carbethoxy-2-cyano)-vinylamino]-N-ethyl-benzoic acid amide, 2,5,6-trichloro-3-[(2-carbo-n-propoxy-2-cyano)-vinylamino]-benzoic acid, 2,5,6-trichloro-3-[(2-carbo-n-propoxy-2-cyano)-vinylamino]-benzoic acid methyl ester, 2,5,6-trichloro-3-[(2-carbo-n-propoxy-2-cyano)-vinylamino]-benzoic acid ethyl ester, 2,5,6-trichloro-3-[(2-carbo-n-propoxy-2-cyano)-vinylamino]-benzoic acid n-propyl ester, 2,5,6-trichloro-3-[(2-carbo-n-propoxy-2-cyano)-vinylamino]-benzoic acid isopropyl ester, 2,5,6-trichloro-3-[(2-carbo-n-propoxy-2-cyano)-vinylamino]-N-methyl-benzoic acid amide, 2,5,6-trichloro-3-[(2-carbo-N-propoxy-2-cyano)-vinylamino]-N-ethyl-benzoic acid amide, 2,5,6-trichloro-3-[(2-carbisopropoxy-2-cyano)-vinylamino]-benzoic acid, 2,5,6-trichloro-3-[(2-carb-isopropoxy-2-cyano)-vinylamino]-benzoic acid methyl ester, 2,5,6-trichloro-3-[(2-carb-isopropoxy-2-cyano)-vinylamino]-benzoic acid ethyl ester, 2,5,6-trichloro-3-[(2-carb-isopropoxy-2-cyano)-vinylamino]-benzoic acid n-propyl ester, 2,5,6-trichloro-3-[(2-carb-isopropoxy-2-cyano)-vinylamino]-benzoic acid isopropoyl ester, 2,5,6-trichloro-3-[(2-carb-isopropoxy-2-cyano)-vinylamino]-N-methyl-benzoic acid amide and 2,5,6-trichloro-3-[(2-carb-isopropoxy-2-cyano)-vinylamino]-N-ethyl-benzoic acid amide.

The active compounds according to the invention engage in the metabolism of the plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended favourably to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds or at verges. The inhibition of growth of herbaceous and woody plants at verges and in the vicinity of overland pipelines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which again counteracts lodging.

In the case of many crop plants, inhibition of the vegetative growth permits denser planting of the crop, so that a greater yield per area of ground can be achieved. A further mechanism of increasing the yield by means of growth inhibitors is based on the fact that the nutrients benefit blossoming and fruit formation to a greater extent, whilst vegetative growth is restricted.

Promotion of vegetative growth can also frequently be achieved with growth regulators. This is of great utility if it is the vegetative parts of the plants which are harvested. Promoting the vegetative growth can, however, also simultaneously lead to a promotion of generative growth, so that, for example, more fruit, or larger fruit, is formed.

Increases in yield can in some cases also be achieved by affecting the plant metabolism, without noticeable changes in vegetative growth. Growth regulators can furthermore produce a change in the composition of the plants so as to bring about better quality of the harvested products. Thus it is possible, for example, to increase the content of sugar in sugar beet, sugar cane, pineapple and citrus fruits or to increase the protein content in soya or cereals.

Parthenocarpous fruit can be formed under the influence of growth regulators. Furthermore, the gender of the flowers can be influenced.

Using growth regulators it is also possible favourably to influence the production or the efflux of secondary plant materials. The stimulation of latex flow in rubber trees may be mentioned as an example.

During the growth of the plant, lateral branching can also be increased, by using growth regulators, through chemical breaking of the apical dominance. There is interest in this, for example, in the case of plant propagation by cuttings. However, it is also possible to inhibit the growth of side shoots, for example to prevent the formation of side shoots in tobacco plants after decapitation and thus to promote leaf growth.

The number of leaves on plants can be controlled, under the influence of growth regulators, so that defoliation of the plants at a desired point in time is achieved. Such defoliation is of interest in order to facilitate mechanical harvesting, for example of grapes or cotton, or to lower the transpiration at a point in time at which the plant is to be transplanted.

Premature shedding of fruit can be prevented by the use of growth regulators. However, it is also possible to promote the shedding of fruit — for example in the case of table fruit — in the sense of a chemical thinning out, up to a certain degree. Growth regulators can also be used to reduce the force required to detach the fruit from crop plants at harvest time so as to permit mechanical harvesting of the plants or facilitate manual harvesting.

Using growth regulators it is furthermore possible to achieve an acceleration or retardation of ripening of the harvest product, before or after harvesting. This is of particular advantage since it is thereby possible to achieve optimum adaptation to market requirements.

Furthermore, growth regulators can in some cases improve the coloration of fruit. In addition, concentrating the ripening within a certain period of time is also achievable with the aid of growth regulators. This provides the preconditions for being able to carry out completely mechanical or manual harvesting in only a single pass, for example in the case of tobacco, tomatoes or coffee.

By using growth regulators it is also possible to influence the latent period of seeds or buds of plants, that is to say the endogenic annual rhythm, so that the plants, such as, for example, pineapple or decorative plants in nurseries, germinate, shoot or blossom at a time at which they normally show no readiness to do so.

Using growth regulators it is also possible to achieve a delay in the shooting of buds or the germination of seeds, for example in order to avoid damage by late frosts in regions where frost is a hazard.

Growth regulators can also produce halophilism in crop plants. This provides the preconditions for being able to cultivate plants on soils containing salt.

Using growth regulators, it is also possible to induce frost resistance and drought resistance in plants.

The active compounds according to the present invention can be converted into the usual formulations, such as solutions, emulsions, suspensions, powders, pastes and granulates. These may be produced in known manner, for example by mixing the active compounds with extenders, that is liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulphoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulphonates, alkyl sulphates and aryl sulphonates as well as albumin hydrolyzation products; and preferred examples of dispersing agents include lignin, sulphite waste liquors and methyl cellulose.

The active compounds according to the invention can be present in the formulations as a mixture with other active compounds, such as fungicides, insecticides, acaricides and herbicides, as well as mixed with fertilisers.

The formulations in general contain from 0.1 to 95% by weight of active compound, preferably from 0.5 to 90% by weight.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They may be used in the customary manner, for example by watering, spraying, atomising, scattering, dusting, foaming, gassing and the like. It is furthermore possible to apply the active compounds by the ultra-low-volume process, to brush plants or parts of plants with the active compound preparation or the active compound itself, or to inject the active compound preparation, or the active compound itself, into the soil. The seed of the plants can also be treated.

The amount of active compound employed can vary within fairly wide ranges. In general, between 0.01 and 50 kg, preferably between 0.05 and 10 kg, of active compound are used per hectare of soil surface.

The preferred space of time within which the growth regulators are used depends on the climatic and vegetative circumstances.

The present invention also provides a plant-growth-regulating composition containing as active ingredient a compound of the present invention in admixture with a solid or liquefied gaseous diluent or carrier or in admixture with a liquid diluent or carrier containing a surface-active agent.

The present invention also provides a method of regulating the growth of plants which comprises applying to the plants, or to a habitat thereof, a compound of the present invention alone or in the form of a composition containing as active ingredient a compound of the present invention in admixture with a diluent or a carrier.

The present invention further provides means of yielding plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

The plant-growth-regulating activity of the compounds of this invention is illustrated by the following biotest Examples.

Example A

Inhibition of growth/barley

Solvent: 10 parts by weight of methanol

Emulsifier: 2 parts by weight of polyoxyethylene sorbitan monolaurate

To prepare a suitable preparation of active compound, 1 part by weight of active compound was mixed with the stated amount of solvent and emulsifier and the mixture was made up to the desired concentration with water.

Young barley plants, in the 2-leaf stage, were sprayed with the preparation of active compound until dripping wet. After the untreated control plants had reached a growth height of about 60 cm, the additional growth of all plants was measured and the inhibition of growth in % of the additional growth of the control plants was calculated. 100% means that growth had stopped and 0% denotes a growth corresponding to that of the control plants.

The active compounds, active compound concentrations and results can be seen from the table which follows.

The active compounds, active compound concentrations and results can be seen from the table which follows:

Table B

| Active compound | Inhibition of growth/soya beans | | Notes |
| --- | --- | --- | --- |
| | Active Compound concentration in % | Inhibition of growth in % | |
| — | — | 0 | — |
| Cl—CH$_2$—CH$_2$—N$^⊕$(CH$_3$)$_3$ Cl$^⊖$ (known) | 0.05 | 0 | — |
| (1) 3-amino-2,5-dichlorobenzoic acid derivative with NH—CH=C(CO—CH$_3$)$_2$ | 0.05 | 35 | — |
| (2) 3-amino-2,5,6-trichlorobenzoic acid derivative with NH—CH=C(CO—CH$_3$)$_2$ | 0.05 | 65 | branched |
| (5) 3-amino-2,5,6-trichlorobenzoic acid derivative with NH—CH=C(CO—CH$_3$)(COO—C$_2$H$_5$) | 0.05 | 75 | branched |

Table A

| Active Compound | Inhibition of growth/barley | |
| --- | --- | --- |
| | Active compound concentration in % | Inhibition of growth in % |
| (Control) | — | 0 |
| Cl—CH$_2$—CH$_2$—N$^⊕$(CH$_3$)$_3$ Cl$^⊖$ (known) | 0.05 | 20 |
| (1) 3-amino-2,5-dichlorobenzoic acid derivative with NH—CH=C(CO—CH$_3$)$_2$ | 0.05 | 35 |

Example B

Inhibition of growth/soya beans
Solvent: 10 parts by weight of methanol
Emulsifier: 2 parts by weight of polyoxyethylene sorbitan monolaurate To prepare a suitable preparation of active compound, 1 part by weight of active compound was mixed with the stated amount of solvent and emulsifier and the mixture was made up to the desired concentration with water.

Young bean plants, at the stage in which the secondary leaves had unfolded completely, were sprayed with the preparations of active compound until dripping wet. After 3 weeks, the additional growth was measured and the inhibition of growth in % of the additional growth of the control plants is calculated. 100% means that growth had stopped and 0% denotes a growth corresponding to that of the control plants.

The preparation of the compounds of the present invention is illustrated by the following preparative Examples.

EXAMPLE 1:

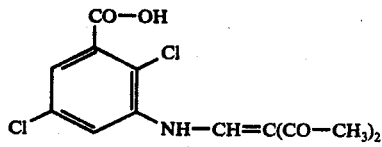

(1)

9.35 g (0.06 mole) of methyl 1-methylcarbonyl-2-ethoxyvinyl ketone were added dropwise to a suspension of 10.3 g (0.05 mole) of 3-amino-2,5-dichlorobenzoic acid in 40 ml of ether. The mixture was stirred for a further 5 hours at room temperature and the precipitate was then filtered off and washed with acetonitrile. 12 g (76% of theory) of 3-[2,2-bis-(methylcarbonyl)-vinylamino]-2,5-dichlorobenzoic acid were obtained in the form of colourless crystals of melting point 244°–246° C.

EXAMPLE 2:

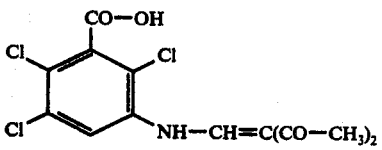

(2)

46.8 g (0.3 mole) of methyl 1-methylcarbonyl-2-ethoxyvinyl ketone were added dropwise to a suspension of 48.1 g (0.02 mole) of 3-amino-2,5,6-trichlorobenzoic acid in 100 ml of toluene. The mixture was heated for 2 hours to 80° C and was then cooled to 10° C, and the precipitate was filtered off. After digesting with acetonitrile, 52 g (74% of theory) of 3-[2,2-bis-(methylcarbonyl)-vinylamino]-2,5,6-trichlorobenzoic acid were obtained in the form of colourless crystals of melting point 242°-244° C.

EXAMPLE 3:

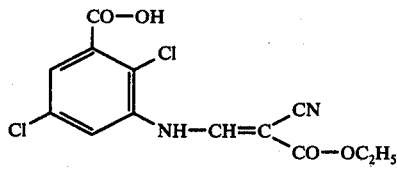
(3)

A mixture of 10.3 g (0.05 mole) of 3-amino-2,5-dichlorobenzoic acid and 33.8 g (0.2 mole) of 2-cyano-3-ethoxy-acrylic acid ethyl ester was heated to 120° C for 2 hours. It was then cooled, acetonitrile was added and the precipitate was filtered off. 10 g (61% of theory) of 3-[(2-carbethoxy-2-cyano)-vinylamino]-2,5-dichlorobenzoic acid were obtained in the form of yellow crystals of melting point 116° C.

The compounds listed in Table 1, which follows, were prepared analogously:

Table 1

| Example No. | R | $R^1$ | $R^2$ | $R^3$ | $R^4$ | $R^5$ | Yield (% of theory) | Melting point (in ° C) |
|---|---|---|---|---|---|---|---|---|
| 4 | —OH | —Cl | —CO—OC$_2$H$_5$ | —CO—CH$_3$ | Cl | H | 64 | 200-202 |
| 5 | —OH | —Cl | —CO—OC$_2$H$_5$ | —CO—CH$_3$ | Cl | Cl | 59 | 222 |
| 6 | —OH | —Cl | —CO—OC$_2$H$_5$ | —CO—OC$_2$H$_5$ | Cl | H | 82 | 190-192 |
| 7 | —OC$_2$H$_5$ | —Cl | —CO—CH$_3$ | —CO—CH$_3$ | Cl | H | 58 | 103 |
| 8 | —OC$_2$H$_5$ | —Cl | —CO—OC$_2$H$_5$ | —CO—CH$_3$ | Cl | H | 64 | 72 |
| 9 | —NH—CH$_3$ | —Cl | —CO—OC$_2$H$_5$ | —CO—CH$_3$ | Cl | H | 61 | 163 |
| 10 | —NH—CH$_3$ | —Cl | —CO—CH$_3$ | —CO—CH$_3$ | Cl | H | 68,6 | 215 |
| 11 | —OH | —H | —CO—CH$_3$ | —CO—CH$_3$ | H | Cl | 98 | >220 |
| 12 | —OH | —H | —CO—OC$_2$H$_5$ | —CO—CH$_3$ | H | Cl | 98 | 162-163 |
| 13 | —OH | —H | —CO—OC$_2$H$_5$ | —CN | H | Cl | 52 | >220 |

It will be understood that the specification and examples are illustrative but not limitative of the present invention and that other embodiments within the spirit and scope of the invention will suggest themselves to those skilled in the art.

What is claimed is:

1. Chlorine-substituted vinylaminobenzoic acid compound of the formula

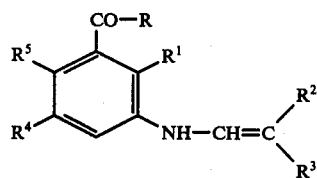
(I)

in which
R is hydroxyl, alkoxy of from 1 to 4 carbon atoms or monoalkylamino of from 1 to 3 carbon atoms,
$R^1$, $R^4$ and $R^5$ are individually selected from hydrogen and chlorine, provided that at least one of $R^1$, $R^4$ and $R^5$ is chlorine, $R^2$ is alkylcarbonyl of from 1 to 4 carbon atoms in the alkyl moiety or carbalkoxy of from 1 to 4 carbon atoms in the alkoxy moiety; and
$R^3$ is cyano, alkylcarbonyl of from 1 to 4 carbon atoms in the alkyl moiety or carbalkoxy of from 1 to 4 carbon atoms in the alkoxy moiety.

2. Chlorine-substituted vinylaminobenzoic acid compound as claimed in claim 1 wherein R is hydroxyl.

3. Chlorine-substituted vinylaminobenzoic acid compound as claimed in claim 1 wherein R is alkoxy of from 1 to 4 carbon atoms.

4. Chlorine-substituted vinylaminobenzoic acid compound as claimed in claim 1 wherein R is monoalkylamino of from 1 to 3 carbon atoms.

5. Chlorine-substituted vinylaminobenzoic acid compound as claimed in claim 1 wherein $R^1$ is chlorine.

6. Chlorine-substituted vinylaminobenzoic acid compound as claimed in claim 1 wherein $R^4$ is chlorine.

7. Chlorine-substituted vinylaminobenzoic acid compound as claimed in claim 1 wherein $R^5$ is chlorine.

8. Chlorine-substituted vinylaminobenzoic acid compound as claimed in claim 1 wherein $R^2$ is alkylcarbonyl of from 1 to 4 carbon atoms in the alkyl moiety.

9. Chlorine-substituted vinylaminobenzoic acid compound as claimed in claim 1 wherein $R^2$ is carbalkoxy of from 1 to 4 carbon atoms in the alkoxy moiety.

10. Chlorine-substituted vinylaminobenzoic acid compound as claimed in claim 1 wherein $R^3$ is cyano.

11. Chlorine-substituted vinylaminobenzoic acid compound as claimed in claim 1 wherein $R^3$ is alkylcarbonyl of from 1 to 4 carbon atoms in the alkyl moiety.

12. Chlorine-substituted vinylaminobenzoic acid compound as claimed in claim 1 wherein $R^3$ is carbalkoxy of from 1 to 4 carbon atoms in the alkoxy moiety.

13. Chlorine-substituted vinylaminobenzoic acid compound as claimed in claim 1 designated 3-[2,2-bis-(methylcarbonyl)-vinylamino]-2,5-dichlorobenzoic acid.

14. Chlorine-substituted vinylaminobenzoic acid compound as claimed in claim 1 designated 3-[2,2-bis-(methylcarbonyl)-vinylamino]-2,5,6-trichlorobenzoic acid.

15. Chlorine-substituted vinylaminobenzoic acid compound as claimed in claim 1 designated 3-[(2-carbethoxy-2-cyano)-vinylamino]-2,5-dichlorobenzoic acid.

16. Chlorine-substituted vinylaminobenzoic acid compound as claimed in claim 1 designated 3-[(2-carbethoxy-2-methylcarbonyl)-vinylamino]-2,5-dichlorobenzoic acid.

17. Chlorine-substituted vinylaminobenzoic acid compound as claimed in claim 1 designated 3-[2-carbethoxy-2-methylcarbonyl)-vinylamino]-2,5,6-trichlorobenzoic acid.

18. Plant-growth regulant compositions comprising an agriculturally acceptable carrier and as an active ingredient at least one chlorine-substituted vinylaminobenzoic acid compound as claimed in claim 1.

19. Method of influencing plant growth which method comprises applying to plants or their habitat an effective amount of a chlorine-substituted vinylaminobenzoic compound as claimed in claim 1.

20. Method as claimed in claim 19 wherein said compound is applied to an area of agriculture in an amount of 0.01 to 50 kg per hectare.

21. Method as claimed in claim 19 wherein said compound is applied to an area of agriculture in an amount of 0.05 to 10 kg per hectare.

22. Method as claimed in claim 19 wherein said compound is applied to inhibit plant growth.

* * * * *